(12) United States Patent
Danelski et al.

(10) Patent No.: US 10,793,411 B2
(45) Date of Patent: Oct. 6, 2020

(54) DEVICE FOR STERILIZING CLOSURES FOR CONTAINERS

(71) Applicant: KHS GmbH, Dortmund (DE)

(72) Inventors: Alexander Danelski, Bad Kreuznach (DE); Thomas Niehr, Bad Münster am Stein Edenburg (DE)

(73) Assignee: KHS GmbH, Dortmund (DE)

( * ) Notice: Subject to any disclaimer, the term of this patent is extended or adjusted under 35 U.S.C. 154(b) by 462 days.

(21) Appl. No.: 15/743,868

(22) PCT Filed: May 19, 2016

(86) PCT No.: PCT/EP2016/061349
§ 371 (c)(1),
(2) Date: Jan. 11, 2018

(87) PCT Pub. No.: WO2017/008941
PCT Pub. Date: Jan. 19, 2017

(65) Prior Publication Data
US 2018/0208445 A1      Jul. 26, 2018

(30) Foreign Application Priority Data
Jul. 15, 2015   (DE) .................. 10 2015 111 446

(51) Int. Cl.
| | | |
|---|---|---|
| *A61L 2/00* | (2006.01) |
| *B08B 3/00* | (2006.01) |
| *B67B 3/00* | (2006.01) |
| *A61L 2/20* | (2006.01) |
| *A61L 2/26* | (2006.01) |

(52) U.S. Cl.
CPC .............. *B67B 3/003* (2013.01); *A61L 2/208* (2013.01); *A61L 2/26* (2013.01); *A61L 2202/23* (2013.01)

(58) Field of Classification Search
CPC ...... B67B 3/003; A61L 2202/23; A61L 2/208; A61L 2/26
USPC .................. 422/292, 300, 302; 134/133, 153
See application file for complete search history.

(56) References Cited

U.S. PATENT DOCUMENTS

| 4,958,649 | A | 9/1990 | Pethö |
| 2006/0159583 | A1* | 7/2006 | Naslund .................. B65B 55/08 422/22 |
| 2011/0061690 | A1* | 3/2011 | Seger ...................... B29C 49/42 134/137 |
| 2012/0260955 | A1* | 10/2012 | Winzinger ............ B29C 49/421 134/43 |

FOREIGN PATENT DOCUMENTS

| DE | 10 2010 025 541 | 12/2011 |
| DE | 10 2010 052 207 | 5/2012 |
| DE | 11 2009 005 221 | 6/2012 |

(Continued)

*Primary Examiner* — Monzer R Chorbaji
(74) *Attorney, Agent, or Firm* — Occhiuti & Rohlicek LLP (57) ABSTRACT

A sterilizing device for sterilizing closures for closing containers has vertically-oriented closure receivers arranged around a circumference of said rotor that moves said closures through a treatment zone between a closure inlet and outlet. One of the closure receivers is provided with said actuating device that at least partially engages the housing for applying, using the actuator, an actuation movement to a closure in said closure receiver. The actuator is movably connected to the opening via a bellows.

11 Claims, 5 Drawing Sheets

(56) References Cited

FOREIGN PATENT DOCUMENTS

| DE | 10 2012 017 986 | 3/2014 |
| DE | 10 2012 107 361 | 5/2014 |
| EP | 2 511 070 | 10/2012 |
| EP | 2 522 485 | 11/2012 |
| EP | 2 848 384 | 3/2015 |
| WO | WO2012/000573 | 1/2012 |

* cited by examiner

DEVICE FOR STERILIZING CLOSURES FOR CONTAINERS

RELATED APPLICATIONS

This is the national stage of international application PCT/EP2016/061349, filed on May 19, 2016, which claims the benefit of the Jul. 15, 2015 priority date of German application DE102015111446.1, the contents of which are herein incorporated by reference.

FIELD OF INVENTION

The invention relates to a device for the bactericidal treatment or sterilization of closures.

BACKGROUND

It is known in the beverage industry to sterilize closures to be used for closing filled containers. These include caps, screw closures, flat caps, crowns, and corks. Known sterilizing agents include $H_2O_2$ vapor or $H_2O_2$ enriched gas.

To promote the effectiveness of the sterilizing agent, it is also known to preheat the closures for example to a temperature in the range between 50° C. and 85° C. After such treatment, the closures are dried with a heated sterile gas. The now-sterilized closures can be used to close containers.

SUMMARY

An object of the invention is to provide a device for the sterilizing and/or bactericidal treatment of closures for closing containers, in particular for the sterilizing of cap-type closures that obviates the disadvantages of the prior art. In particular, the device provides for the controlled release of closures that are tilted and/or that are stuck in the closure receiver.

In one aspect of the invention, an apparatus for sterilizing closures for closing containers has a vertically-oriented closure receiver that has an assigned actuating device that engages at least partially in the housing for the purpose of applying an actuation movement, by means of an actuator, to a closure received in the closure receiver. The actuator is movably connected to an opening in the housing through a bellows.

A particular advantage arises because closures that stick or are tilted in the closure receiver can be released in a controlled manner by an actuation movement initiated on the closure by an actuator.

In some embodiments, the actuating device extends along a longitudinal axis that is essentially parallel to the machine axis and arranged radially at a distance from the rotor. The actuating device can also be arranged above the closure outlet in such a way that the actuator subjects a closure received in the closure receiver to an actuation movement.

Preferably, an actuator's impulse segment initiates an actuation movement. The actuator's impulse segment forms an acute angle relative to a closure axis. Preferably, this acute angle is between 25° and 85°.

According to a preferred embodiment, the actuator comprises first and second carrier segments, with the actuator's second carrier segment being connected to the actuator's impulse segment.

In some embodiments, actuator impulse segments are arranged at the second carrier segment. In yet other embodiments, carrier segments are formed as bars.

In other embodiments, the second carrier segment connects to the first carrier segment. In such embodiments, the first carrier segment and the second carrier segment are arranged at an angle to one another.

In other embodiments, the actuator's first carrier segment is at least partially accommodated in the bellows and also movable as it is guided through the opening of the housing, preferably in a fluid-tight manner.

Among such embodiments are those in which a first side of the first carrier segment is movably guided through the opening of the housing and with a second side thereof is guided through a guide segment of the bellows and is accommodated mechanically fixed in a guide segment of the bellows.

In some embodiments, the actuator is accommodated with an impulse segment thereof at least partially in a bellows and is movably as it is guided through the opening of the housing, preferably in a gas-tight and/or liquid-tight manner. Among these are embodiments that assign a separate bellows to each impulse segment. The individual impulse segments are guided via separate openings through the housing and are movably connected via their corresponding bellows.

As used herein, "essentially" refers to deviations from an exact value by ±10%, preferably ±5%, and/or deviations that are not significant for function.

As used herein, "closure" includes closures of widely differing kinds, including cap-type closures, such as screw closures, flat caps, crown corks, etc.

Further embodiments, advantages, and possible applications of the invention are also derived from the following description of exemplary embodiments and from the figures. In this context, all the features described and/or represented as images are in principle, individually or in any desired combination, the object of the invention, regardless of their connection in the claims or reference to them. The contents of the claims are likewise made a constituent part of the description.

BRIEF DESCRIPTION OF THE DRAWINGS

The invention is described in greater detail hereinafter on the basis of the figures in relation to an exemplary embodiment. The figures show.

DETAILED DESCRIPTION

Figure 1:
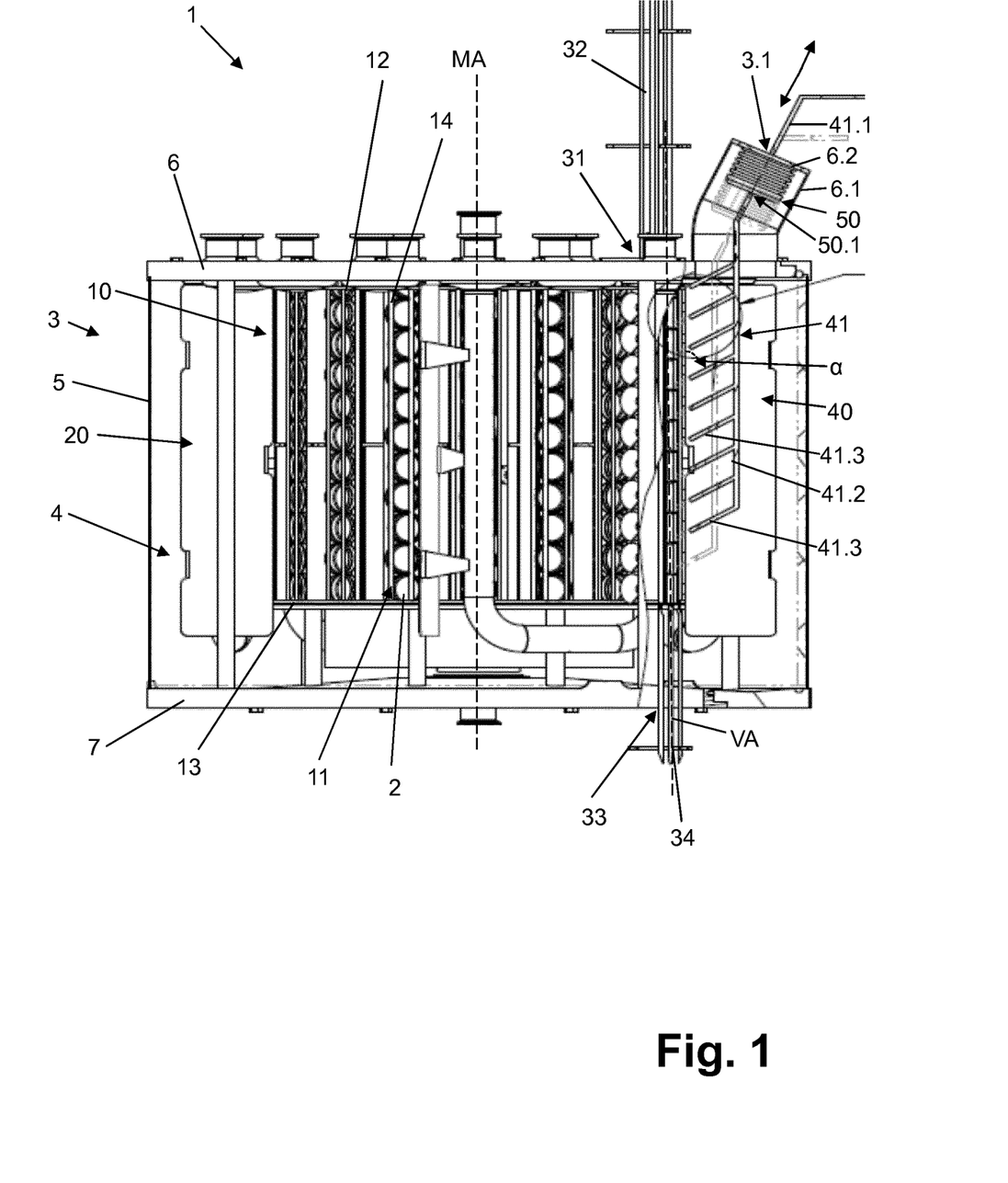
FIG. 1 shows a side view of a sterilizing device.
Figure 2:
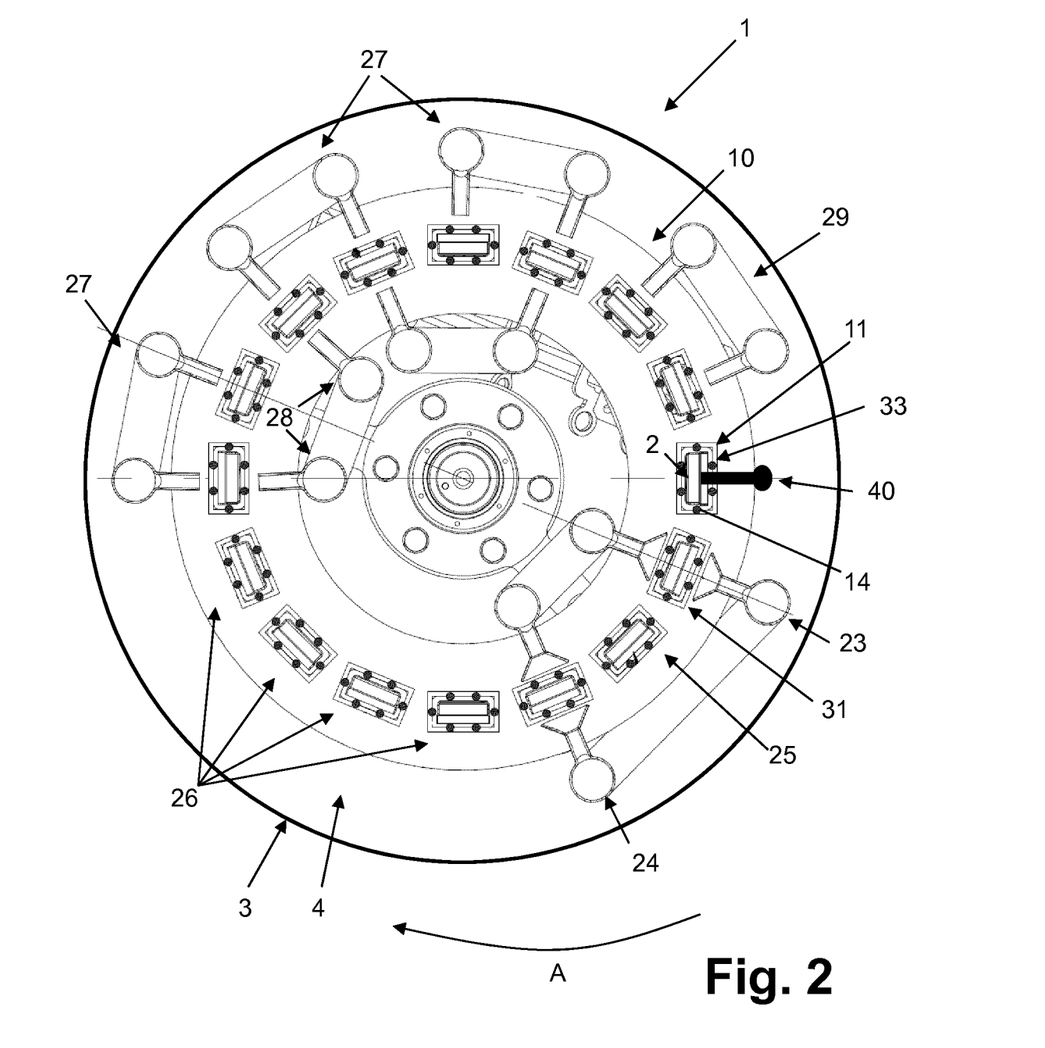
FIG. 2 shows a top view of the device shown in FIG. 1.

FIGS. 1 and 2 show a sterilizing device 1 that sterilizes closures 2. Such closures include caps, screw caps, sport caps, flat caps, or crown corks, etc., all of which are used for closing containers, including bottles. The sterilizing device 1 is arranged upstream of a closing machine for closing of containers. Sterilized closures 2 are conveyed under sterile conditions from the sterilizing device 1 to the closing machine.

Referring to FIG. 1, the sterilizing device 1 includes a polygonal or cylindrical housing 3 that surrounds a vertical machine-axis MA. In some embodiments, the housing 3 is hexagonal.

With the exception of a closure inlet 31 and a closure outlet 33, the housing's interior 4 is closed against the environment in a fluid-tight manner. This tight closure is provided by the combination of a circumferential wall 5 surrounding the machine axis MA, an upper housing wall 6, and a lower housing wall 7. Some embodiments include one or more inspection windows in the circumferential wall 5. In other embodiments the circumferential wall 5 is itself transparent material.

A rotor 10 in the interior 4 of the housing 3 rotates about the machine axis MA. In the illustrated embodiment, the rotor 10 is a hollow drum shaped like a circular cylinder that concentrically surrounds the machine axis MA. The drum has a drum casing with a cage-like structure formed by closure receivers 11. Each closure receiver 11 receives a row of closures 2.

Each closure receiver 1 is oriented with its longitudinal extension parallel or essentially parallel to the machine axis MA. Each closure receiver 11 has an upper end and a lower end, both of which are open. The upper end receives closures 2; the lower end discharges closures 2.

The closure receivers 11 are distributed at uniform angular distances around the machine axis MA at the circumference of the rotor 10. Together, they form the cage-like or lattice-like structure. This structure forms an inherently stable casing for the rotor 10.

The upper end of each closure receiver 11 is secured to an upper carrier element 12. Similarly, the lower end of each closure receiver 11 is secured to a lower carrier element 13. The lower end is secured in such a way that the lower carrier element 13 does not close the opening at the lower end.

In some embodiments, a grid of closure guide rails 14 defines a closure receiver 11. In other embodiments, the closure receivers 11 are milled parts with correspondingly shaped contours.

The closure guide rails 14 are rods or bars that are spaced apart from one another and that are parallel to the machine axis MA. The guide rails 14 form between them a receiver space for receiving a row of closures 12. The closures 2 in each closure receiver 11 form a single-track row that extends parallel to the machine axis MA along a closure axis VA. The guide rails 14 are thin enough so that the closures 2 are relatively free and open to the environment when they are in the closure receiver 11.

The closure receivers 11 hold the closures 2 in a predetermined orientation relative to the machine axis MA. In the illustrated embodiment, the closures 2 are oriented so that a surface-normal vector to the closure 2 is in the radial direction and the open side of each closure 2 faces radially outward toward the housing wall 6.

The lower carrier element 13 and the rotor 10 are mounted on a bearing on the underside of the sterilizing device 1. A motor rotates the rotor 10 around the machine axis MA in a circumferential direction A.

The rotor 10 rotates in discrete angular steps of uniform angular extent. The number of degrees of this extent shall be called the "step size." The amount of time between movements of the rotor 10 shall be called the "standstill interval."

The sterilizing device 1 includes application stations 20 in the housing's interior 4 within the sterilizing device's treatment chamber. These applications stations 20 do not rotate with the rotor. The step size fixes the positions of the application stations 20 on the inner and outer sides of the rotor 10 as shown in FIG. 2. In particular, application stations 20 are separated from each other by an integer multiple of the step size.

Application stations 20 include first and second sterilizing stations 23, 24, drying stations 28, activation stations 27, and cooling stations 29. These application stations 20 are oriented with their longitudinal extensions parallel to the machine axis MA.

On of the application stations 20 has an actuating device 40 that has an actuator 41. At least one vertically oriented closure receiver 11 is at the actuating device 40.

The actuating device 40 at least partially engages the housing 3 for the purpose of initiating an actuation movement by the actuator 41 that acts on at least one closure 2 received in the closure receiver 11.

As can be seen from FIGS. 1 and 2, the actuating device 40 extends along a longitudinal axis that is essentially parallel to the machine axis MA. FIG. 2 shows a preferred disposition of the actuating device 40 between the first sterilizer station 23 and the cooling station 29 such that if one were to proceed in the circumferential direction A starting from the cooling station 29 one would encounter the actuating device 40 radially offset from the rotor 10 prior to reaching the first sterilizer station 23.

Referring to FIG. 1, a wall segment 6.1 of the upper housing wall 6 projects obliquely upward to an opening 3.1 at a distal end thereof. The wall segment 6.1 defines an axis that forms an oblique angle relative to the machine axis MA. The wall segment 6.1 and the upper wall 6 are integral with each other and form one piece with the housing 3. The bellows 50 is arranged beneath the opening 3.1. A portion of the actuator 41 passes through the bellows 50 and through the opening 3.1 of the housing 3.

In an alternative embodiment, a housing cover 6.2 forms a fluid-tight seal over the wall segment 6.1. In such embodiments, the housing cover 6.2 includes the opening 3.1. The actuator 41 is movably guided to the outside from the interior 4 of the housing 3, as indicated by the double-arrow in FIG. 1. An actuator motor moves the actuator 41.

Figure 3:
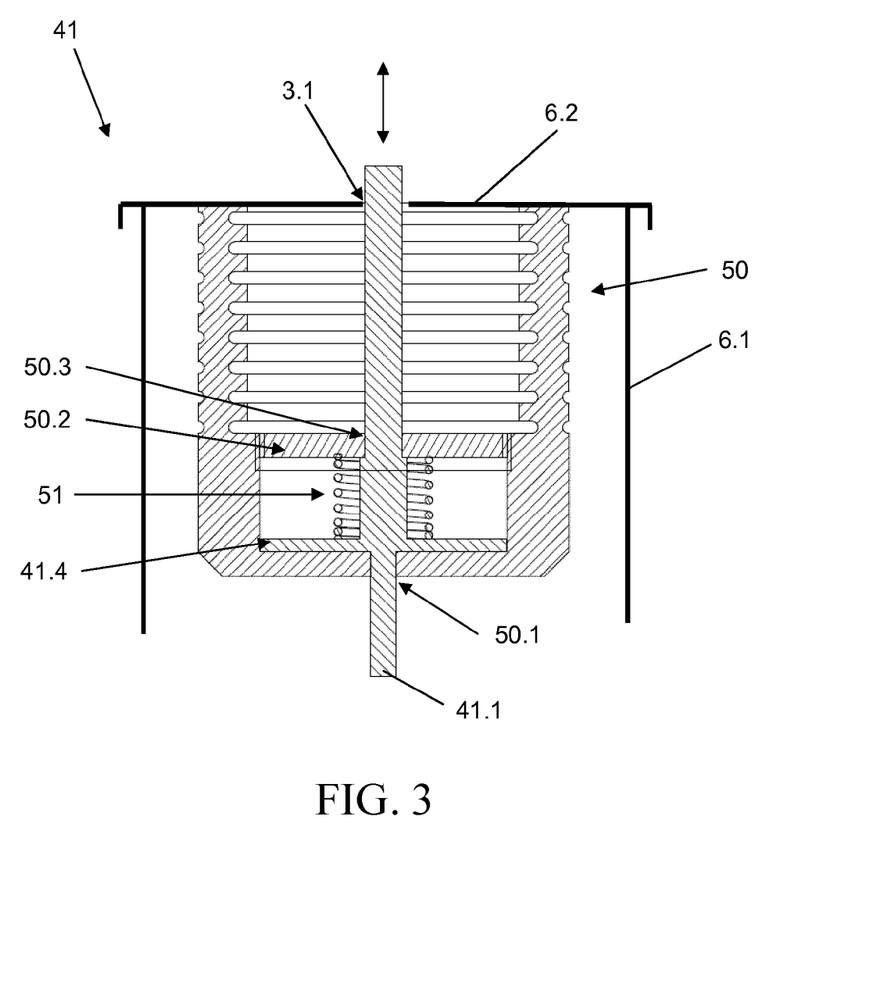
FIG. 3 shows a side view of a section of the device shown in FIG. 1.

Referring now to FIG. 3, on the underside of the housing cover 6.2, the bellows 50 is connected securely so that it is tightly sealed to the housing cover 6.2. This can be done, for example, by the housing cover 6.2 comprising on its inner side, in the region the opening 3.1, a flange collar onto which the bellows 30 is pushed and secured, for example, by a sleeve. As a result, the bellows 50 surrounds the actuator 41 in the region of the opening 3.1. Yet, the actuator 41 remains movable through the opening 3.1.

To promote this isolation and movability, the bellows 50 provides, on a side facing away from the housing cover 6.2, a guide segment 50.1 that penetrates the bellows 50. It is through this guide segment 50.1 that the actuator 41 is introduced.

Arranged in the region of the guide segment 50.1, or on it, is the actuator 41 itself. The actuator 41 is secured and sealed tightly to the bellows 50 in the manner described in greater detail in FIG. 3.

Referring to FIG. 1, the actuator 41 comprises a first carrier segment 41.1 and a second carrier segment 41.2. The first carrier segment 41.1 extends along a direction that forms an angle relative to the machine axis MA. The second carrier segment 41.2 connects to the first carrier segment 41.1. Unlike the first carrier segment 41.1, the second carrier segment 41.2 is essentially parallel to the machine axis MA. The first carrier segment 41.1 and the second carrier segment 41.2 therefore do not form a straight line. As a result of the angle between them, the actuator 41 initiates both a vertical and a radial actuation movement. The resultant actuating movement extends along a direction that makes an oblique angle relative to the closure axis VA of the closure receiver 11 that is assigned to the actuating device 40.

Impulse segments 41.3 branch off the second carrier segment 41.2 like tines of a comb. In some embodiments, the carrier segments 41.1, 41.2 and the impact segments 41.3 form a one-piece actuator 41. In other embodiments, the impact segments 41.3 are separate components that are arranged at the second carrier segment 41.2 but nevertheless detachable from it. For example, an impact segments 41.3 might be threaded so that it can be screwed on the second carrier segment 41.2.

The number of impact segments 41.3 and their geometric parameters can be adjusted to accommodate different closure types and different numbers of closures 2 in a closure receiver 11. Examples of geometric parameters that can be adjusted include distances between impact segments 41.3, lengths, diameters, or cross-sections of the impact segments 41.3, and the material used to make the impact segments 41.3.

In a preferred embodiment, the number of impact segments 41.3 corresponds to the maximum number of closures 2 that can be received in a closure receiver 11. A particular advantage of such an embodiment is that one separate impact segment 41.3 can be assigned to each closure 2 in the closure receiver 11.

In addition to this, it can be advantageous if the individual impact segments 41.3 enclose an acute angle $\alpha$ with the closure axis VA. Preferably, the acute angle $\alpha$ lies between 25° and 85°. A particularly useful choice for the acute angle $\alpha$ is an angle at or close to 45°. To further advantage, the individual impact segments 41.3 span a common plane in which they are arranged.

At the initiation of an actuation movement onto the actuating device 40, the bellows 50 and the actuator 41 move together, at least in its guide segment 50.1. As the actuator 41 moves, the bellows 50 maintains a separation between the atmosphere within the housing's interior 4 and the atmosphere prevailing outside the housing 3.

It is possible to include, among the application stations 20, dwell stations at which no processing takes place. At such locations, the sterilizing agent applied onto the closures 2 in the application station 20 can take effect during a standstill interval. After having been bathed in sterilizing agent for one standstill interval, the closures 2 are advanced by one step size to a further application station 20, in order, for example, to be subjected to a further application of sterilizing agent.

In the example shown in FIGS. 1 and 2, the closure inlet 31 is assigned to the first sterilizing station 23 above the movement path of the closure receiver 11. The closure outlet 33 is formed through the lower housing wall 7 beneath the movement path of the closure receiver 11 that is at the actuating device 40.

The sterilizing device 1 also includes first and second closure conveyors 32, 34. The first closure conveyor 32 brings closures to be sterilized to the closure inlet 31. The second closure conveyor 34 receives sterilized closures 2 from the closure outlet 33. In the illustrated embodiment, both the first and second closure conveyors 32, 34 are vertical. This permits gravity alone to move the closures 2. The first and second closure conveyors 32, 34 are formed by guide rails that receive and guide the closures 2 between them. To avoid recontamination of sterilized closures 2, a casing filled with sterile gas at a slight overpressure surrounds the second closure conveyor 34.

The first closure conveyor 32 guides closures toward a lower end from which the closures drop through the upper housing wall 6 into the closure inlet 31. These closures 2 already have an orientation that corresponds to their orientation in the closure receivers 11.

The second closure conveyor 34 receives sterilized closures that have dropped through the closure outlet 33 in response to movement by the actuating device 40. It then conveys these sterilized closures 2 to a closing machine.

The angular separation between the closure inlet 31 and the closure outlet 33 is an integral number of step sizes that corresponds to how many closure receivers 11 are present on the rotor 10. As a result, during each standstill interval, a closure receiver 11 will have its upper open end at the closure inlet 31 waiting to receive closures 2 and another closure receiver 11 will have its lower open end at the closure outlet 33 waiting to discharge closures 2. Preferably, the angular separation between the closure inlet 31 and the closure outlet 33 is the largest multiple of step size that is below 360°. This will promote the longest possible treatment time. A suitable angle is 330°.

Preferably, the closure inlet 31 and the closure outlet 33 are separated by one step size. In particular, the closure inlet 31 is arranged above the first sterilizing station 23 and the closure outlet 33 is arranged one step size upstream of the first sterilizing station 23.

In operation, the rotor 10 moves in steps equal to one step size. These movements are separated by standstill intervals during which the rotor 10 is stationary. During a standstill interval, an empty closure receiver 11 waits beneath the closure inlet 31 as the first closure conveyor 32 fills it with closures 2 that are to be sterilized. Another closure receiver 11 waits above the closure outlet 33 to discharge its sterilized closures 2 into the second conveyor 34. The remaining closure receivers 11 are processed at their respective application stations 20.

FIG. 3 shows a section of the housing wall segment 6.1 that is covered by a housing cover 6.2. The housing cover 6.2 has the opening 3.1 through which the first carrier segment 41.1 travels as it moves outward from the housing 3. The bellows 50 is secured to the underside of the housing cover 6.2 to form a fluid tight seal.

The first carrier segment 41.1 has a first side and a second side. The first side moves through the opening 3.1. The second side passes through and is secured to a guide segment 50.1. As a result, when the first carrier segment 41.1 moves, the bellows 50 also moves. The bellows 50 thus maintains separation between the interior and exterior of the housing 3 even while the actuator 41 moves.

A guide 50.2 arranged in the interior of the bellows 50 is configured as an annular piston fixed to the bellows 50. The guide 50.2 has a passage 50.3 whose size and shape conform to the first carrier segment 41.1 that passes therethrough.

In the illustrated embodiment, the first carrier segment 41.1 includes a wing segment 41.4 that extends at an approximate right angle radially outwards from the actuator 41, which is fixed securely to the bellows 50 and also sealed tight. A helical pressure spring 51 between the wing segment 41.4 and the guide 50.2 is held under a defined pre-tension around the actuator 41.

Figure 4:
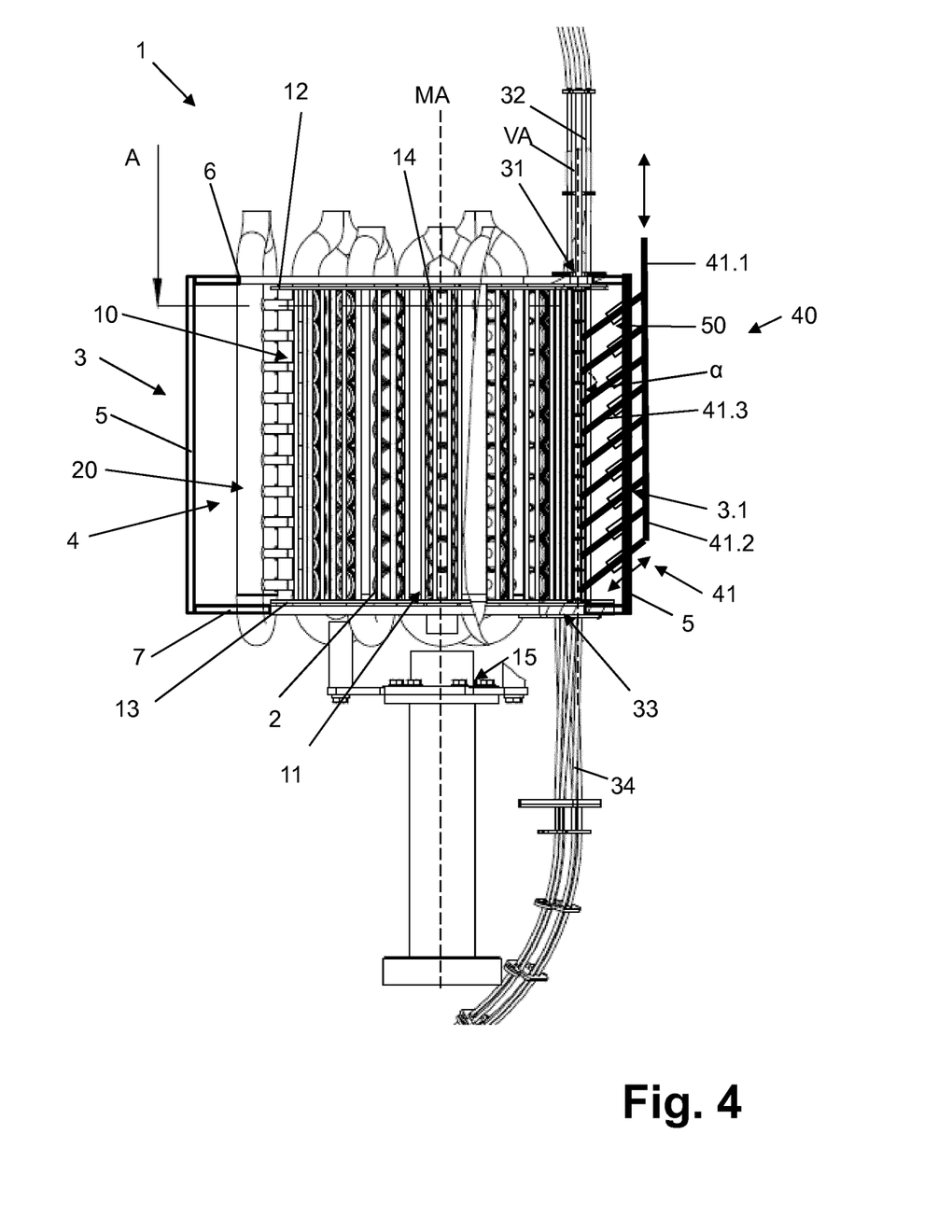
FIGS. 4 and 5 show additional embodiments of a sterilizing device.

FIG. 4 shows in a lateral schematic representation a further embodiment of the sterilizing device 1 in which the actuator 41 comprises a plurality of impulse segments 41.3, assigned to each of which is a separate bellows 50 and a separate opening 3.1 in the housing's circumferential wall 5. Each bellows 50 surrounds an impulse segment 41.3 or at least partially accommodates an impulse segment 41.3.

Each impulse segment 41.3 is guided so that it moves through its own separate opening 3.1. Each impulse segment 41.3 is also connected to its corresponding opening 3.1 through its bellows 50. The actuator 41 with its impact segments 41.3 is movably guided, in particular from the outside, through the plurality of openings 3.1, into the interior 4 of the sterilizing device 1.

Each bellows 50 has a first side thereof fixed to and sealed tightly to the inner side of the circumferential wall 5. Each impact segment 41.3 can be movably guided through its corresponding opening 3.1. Accordingly, each impact segment 41.3 is also configured to move relative to the first side of its corresponding bellows 50. The impact segments 41.3 are mechanically fixed in the guide segments 50.1 of their corresponding bellows 50 such that, at the initiation of an actuation movement, each guide section 50.1 moves with its corresponding impact segment 41.3.

In some embodiments, the bellows completely surrounds its corresponding impact segment 41.3 in the housing's interior. In such embodiments, the bellows 50 does not have a receiving segment 50.1.

The number of impact segments 41.3 and their geometric parameters can be adjusted to accommodate different closure types and different numbers of closures 2 in a closure receiver 11. Examples of geometric parameters that can be adjusted include distances between impact segments 41.3, lengths, diameters, or cross-sections of the impact segments 41.3, and the material used to make the impact segments 41.3.

In a preferred embodiment, the number of impact segments 41.3 corresponds to the maximum number of closures 2 that can be received in a closure receiver 11. A particular advantage of such an embodiment is that one separate impact segment 41.3 can be assigned to each closure 2 in the closure receiver 11.

The embodiment shown in FIG. 4 first and second carrier segments 41.1, 41.2 that extend along a straight line. As such, they differ from those in the embodiment shown in FIG. 1, in which the first and second carrier segments 41.1, 41.2 form an angle relative to each other.

An actuator motor causes the actuator 41 to engage in a controlled actuation movement. The actuation movement has a radial and vertical component so that the resultant movement is oblique relative to the closure axis VA, as shown by the double arrow.

In the embodiment shown in FIG. 4 it is advantageous if the individual impact segments 41.3 and the closure axis VA define an acute angle α that lies preferably between 25° and 85°, for particular preference close to 45°. It is also advantageous for the individual impact segments 41.3 to span a common plane in which they are arranged.

Figure 5:
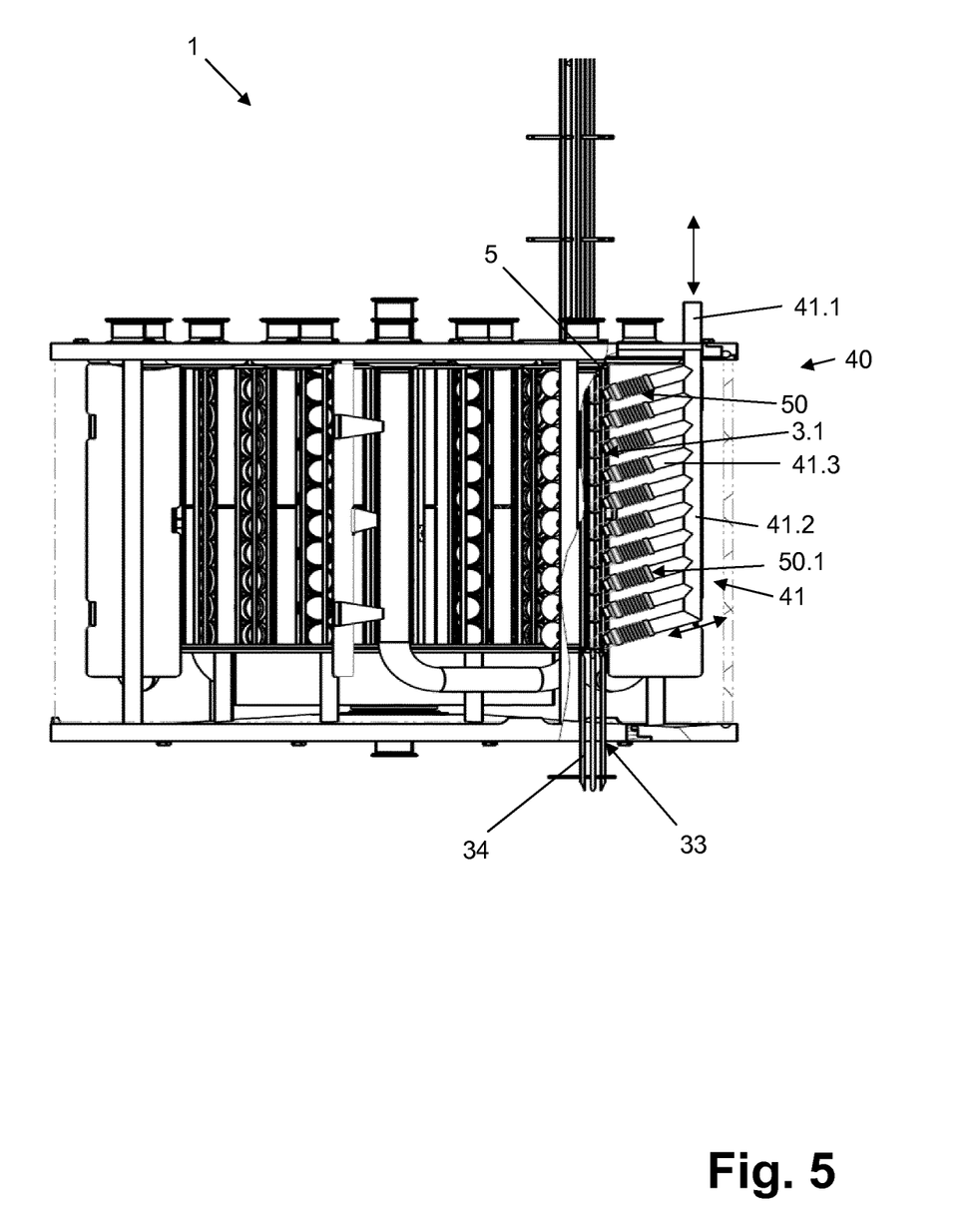

FIG. 5 shows yet another embodiment of a sterilizing device 1 that has bellows 50 outside the circumferential wall 5 rather than inside the housing 3. Each bellows 50 is secured with its first side to its corresponding opening 3.1 through the circumferential wall 5. Each bellows 50 is secured at its first side by a sleeve to a flange-type collar provided at the corresponding opening 3.1. Each impact segment 41.3 is movably guided through its corresponding opening 3.1. Each impact segment 41.3 is also configured to be movable relative to the first side of its bellows 50. Each impact segment 41.3 is accommodated in and mechanically fixed to a guide segment 50.1 of its corresponding bellows 50 such that the guide segment 50.1 moves together with the impact segment 41.3 at actuation.

The actuating device 40 of the embodiment shown in FIG. 5 can also be used to initiate a controlled actuation movement onto the actuator 41 by interacting with an actuator motor, not represented in greater detail, in such a way that, at the initiation of an actuating movement onto the actuator 41, both a vertical as well as a radially configured actuation movement is initiated, i.e. an actuating movement running obliquely to the closure axis VA, at least of the actuator impulse segments 41.3 in the direction of the closure receiver 11 assigned to the actuating device 40. The movement capability of the actuator 41 is represented schematically in FIG. 5 by a double arrow.

The invention has been described several exemplary embodiments. It is understood that numerous modifications and variations are possible without thereby departing from the inventive concept on which the invention is based.

Having described the invention and a preferred embodiment thereof, what we claim as new and secured by Letters Patent is:

1. An apparatus comprising a sterilizing device for sterilizing closures for closing containers and a housing that accommodates said sterilizing device, wherein said housing comprises an opening, wherein said sterilizing device comprises a transport system, closure receivers, a closure inlet, a closure outlet, an actuating device, an actuator, and a bellows, wherein said transport system moves said closures through a treatment zone in which said closures are at least one of sterilized and dried, wherein said transport system comprises a rotor that rotates about a machine axis, wherein said closure receivers are vertically oriented and arranged around a circumference of said rotor, wherein said rotor moves said closures through said treatment zone between said closure inlet and said closure outlet, wherein a first closure receiver from said closure receivers is provided with said actuating device, wherein said actuating device at least partially engages said housing for applying, using said actuator, an actuation movement to a closure in said closure receiver, wherein said actuator is movably connected to said opening via said bellows.

2. The apparatus of claim 1, wherein said actuating device extends along a longitudinal axis that is parallel to said machine axis and wherein said actuating device is radially offset from said rotor.

3. The apparatus of claim 1, wherein said actuating device is arranged above said closure outlet and wherein said actuator subjects a closure in said first closure receiver to an actuation movement.

4. The apparatus of claim 1, wherein said actuator comprises an impact segment that initiates an actuation movement, wherein said impact segment encloses an angle relative to a closure axis of said first closure receiver, and wherein said angle is between twenty-five degrees and eighty-five degrees.

5. The apparatus of claim 1, wherein said actuator comprises impact segments, a first carrier segment, and a second carrier segment, wherein said second carrier segment connects to said impact segments and wherein said impact segments initiate an actuation movement.

6. The apparatus of claim 1, wherein said actuator comprises a first and second carrier segments and a plurality of impact segments arranged at said second carrier segment and wherein said impact segments initiate actuation movement.

7. The apparatus of claim 1, wherein said actuator comprises an impact segment and first and second carrier segments, one of which is formed as a bar, wherein said second carrier segment connects to said impact segment and wherein said impact segment initiates an actuation movement.

8. The apparatus of claim 1, wherein said actuator comprises an impact segment, a first carrier segment, and a second carrier segment, wherein said second carrier segment connects to said impact segment, wherein said impact segment initiates an actuation movement, wherein said second carrier segment connects to said first carrier segment, and wherein said first and second carrier segments are arranged at an angle to one another.

9. The apparatus of claim 1, wherein said actuator comprises impact segments, a first carrier segment, and a second carrier segment, wherein said second carrier segment connects to said impact segments, wherein each of said impact segments initiates an actuation movement, wherein said bellows at least partially accommodates said first carrier segment, and wherein said actuator is movably guided through said opening in a fluid-tight manner.

10. The apparatus of claim 1, wherein said bellows comprises a guide section, wherein said actuator comprises impact segments, a first carrier segment having first and second sides and a second carrier segment, wherein said second carrier segment connects to said impact segments, wherein said first carrier segment is movably guided on said first side through said opening, wherein said second side is guided through said guide section, and wherein said second side is mechanically fixed in said guide section.

11. The apparatus of claim 1, wherein said actuator comprises an impact segment that initiates an actuation movement, wherein said bellows at least partially accommodates said impact segment, and wherein said impact segment is movably guided through said opening in a fluid-tight manner.

\* \* \* \* \*